Figure 1:
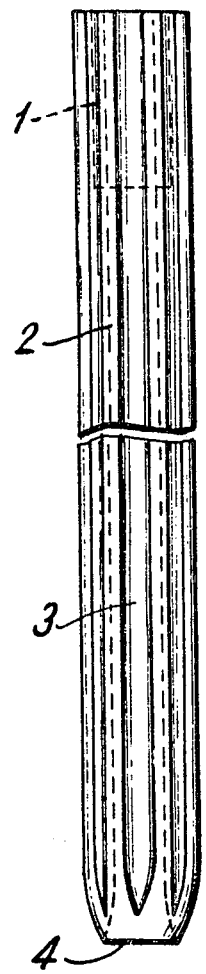

United States Patent [19]

Otte et al.

[11] 4,446,857

[45] May 8, 1984

[54] MEDULLARY NAIL AND PROCESS FOR THE PRODUCTION THEREOF

[75] Inventors: Wolf-Dieter Otte; Heinz Otte, both of Volkach, Fed. Rep. of Germany; Siegfried Schider, Reutte; Otto Wiesner, Ruette-Muehl, both of Austria

[73] Assignee: Schwarzkopf Development Corporation, New York, N.Y.

[21] Appl. No.: 351,105

[22] PCT Filed: Sep. 4, 1979

[86] PCT No.: PCT/US79/00708

§ 371 Date: May 9, 1980

§ 102(e) Date: May 9, 1980

[87] PCT Pub. No.: WO80/00533

PCT Pub. Date: Apr. 3, 1980

[30] Foreign Application Priority Data

Sep. 4, 1978 [AT] Austria ................................ 6368/79

[51] Int. Cl.³ .............................................. A61F 5/04
[52] U.S. Cl. ............................ 128/92 BC; 128/92 BA
[58] Field of Search ............ 128/92 B, 92 BC, 92 CA, 128/92 C, 92 BA, 92 R

[56] References Cited

U.S. PATENT DOCUMENTS

| | | | |
|---|---|---|---|
| Re. 28,502 | 8/1975 | Burstein et al. | 128/92 BC |
| 3,178,728 | 4/1965 | Christensen | 128/92 C |
| 3,605,123 | 9/1971 | Hahn | 3/1 |
| 3,643,658 | 2/1972 | Steinemenan | 128/92 B |
| 3,893,196 | 7/1975 | Hochman | 128/92 BC |
| 4,040,129 | 8/1977 | Steinemann et al. | 3/1.9 |
| 4,103,683 | 8/1978 | Neufeld | 128/92 BC |
| 4,261,350 | 4/1981 | Branemark et al. | 128/92 BC |

FOREIGN PATENT DOCUMENTS

| | | |
|---|---|---|
| 0008758 | 8/1979 | European Pat. Off. . |
| 913228 | 6/1954 | Fed. Rep. of Germany . |
| 246326 | 4/1966 | Fed. Rep. of Germany . |
| 2361933 | 1/1976 | Fed. Rep. of Germany . |
| 2701279 | 7/1977 | Fed. Rep. of Germany . |
| 2609723 | 7/1977 | Fed. Rep. of Germany . |
| 2288506 | 5/1976 | France . |
| 2342710 | 9/1977 | France . |

OTHER PUBLICATIONS

"The Metal Tantalum", 1939, Fansteel Metallurgical Corp., North Chicago, Ill.

Primary Examiner—C. Fred Rosenbaum
Assistant Examiner—C. W. Shedd
Attorney, Agent, or Firm—Morgan, Finnegan, Pine, Foley & Lee

[57] ABSTRACT

There is provided a medullary nail having a hollow body provided with a plurality of longitudinal concave zones (3) in the outer surface and contiguous zones of annular form (2) and having a cutter (4) at one end. The body is of tantalum, an alloy thereof containing more than 50% tantalum, niobium, or an alloy thereof containing more than 50% niobium and is provided with a female thread (1) at the end opposite the cutter (4) and is anodically oxidized and the wall thickness is approximately the same over the entire length.

There is also provided a process for making the nail by rolling a sintered body of tantalum or niobium to form a sheet which is then shaped into a slotted tubular form and welded and then rolling, forging or pressing to form the concave zones (3) or making the tubular form by extruding it from sheet of sintered body material and then proceeding as above stated.

3 Claims, 2 Drawing Figures

U.S. Patent  May 8, 1984  4,446,857

MEDULLARY NAIL AND PROCESS FOR THE PRODUCTION THEREOF

The invention relates to a medullary nail for the fixation of fractures and which consists of an approximately tubular body provided with longitudinal grooves in the outer surface and having a circular cutting surface at one end, and, as well, to a process for making the same.

At the present, standardized medullary nails according to Küntscher are used predominantly in bone surgery. The nails have a slotted tubular form of cloverleaf cross-section or V-shaped cross-section and are provided with a ring-shaped cutter at one end. A slot-type eye at the opposite end of the nail provides the means to attach an extraction hook thereto, thus permitting the nail to be pulled out of the bone. A certain spring action is known to be achieved by the longitudinal slits in the nail, whereby the driven nail is pressed laterally against the bone tissue. However, the mechanical hold or grip in the bone marrow, and, in particular, the rotation stability, is insufficient where such medullary nails are employed.

A number of other prior publications are known which show other forms of medullary nails. Thus, DT-PS No. 913,228 describes longitudinally slotted medullary nails which have a variety of cross-sections. The strength of such nails has, in part, been increased by "embossing" of individual wall regions or portions. A medullary nail according to French Patent Application No. 2,288,506 is a solid round rod provided with longitudinal grooves which are semicurcular in profile. A medullary nail described in French Patent Application No. 2,342,710 for the retention of a bone plate has a tubular form and is provided on the outer surface with longitudinal grooves having a rounded profile milled therein.

In DT-AS No. 2,361,933 there is disclosed a tubular medullary nail which has longitudinal elevations on its outer surface, terminating in the cutting surface at one end of the tube. The elevations taper outwardly, sharply forming tips and bone material is cut out by these tips as the medullary nail is being driven into the bone and is deposited in the cavities between adjacent tips. An advantage of this form of medullary nail over the Küntscher nail, for instance, is the better hold or grip and the greater rotation stability in the bone. It is regarded as a disadvantage that in driving in or inserting such a nail considerable amounts of bone material are cut out and in the region of the pointed longitudinal elevations an adversely high pressure is exerted by the nail on the bone material, thereby increasing the danger of splintering and fissuring. The nail has an extraction slit at one end, or alternatively, a female thread into which a corresponding extraction tool is screwed.

Medullary nails must be made of materials of high tensile and bending strength, sufficient elongation and the highest possible corrosion stability, as well as tissue compatibility. To this day, they are made, as a rule, of chromium, molybdenum, and nickel alloyed steels. Although such materials must be considered as being among the stainless steels, when used in the living body, there occur therewith most undesirable chemical corrosion reactions, e.g. stress corrosion, cracking and pitting. Consequently, the implants are damaged and become useless. In addition, due to the reactions between the implant material and organic tissue the tissue per se is damaged and healing of the fracture is made difficult or impossible. Such phenomena are known as metallosis.

Many attempts have, therefore, been made to get away from the mentioned steel grades of materials for the making of medullary nails and to use in their stead, for example, alloys of cobalt or titanium. It has been proposed also to improve the mentioned materials superficially by oxidizing, nitriding or carbonizing them or by applying ceramic coating or layers thereon.

In connection with the metallosis phenomena, occasionally tantalum has been mentioned in the past, because of its high tissue compatibility. The prevailing opinion is, however, that because of its low strength tantalum can be used only where the ductility of the material is of prime importance, such as, for example, in the form of fine wires and meshes. In addition, the high specific gravity and the high cost of tantalum are usually given as reasons why tantalum cannot be used more widely as an implant material.

It is customary to increase the strength properties of metallic materials by hot and cold working, such as rolling and drawing. However, it is well-known that metals of high melting point, such as niobium and tantalum are deformable to a comparatively very limited. Moreover, attempts to increase the strength of such metals by the addition of substances thereto result in the undesirable property that an increase in strength thereto and deformation thereof are usually accompanied by strong embrittlement. Besides, for reasons of tissue compatibility, the addition of extraneous substances to improve the mechanical properties is possible only to a very limited extent.

The problem in connection with the present invention was to create a medullary nail which, on the one hand, does not have the described disadvantages of existing designs, such as an insufficient hold or grip in the marrow. A lack of rotation stability or excessive local pressure load on the bone tissue. On the other hand, the problem also included the creation of a medullary nail employing metals actually known to be tissue compatible, such as tantalum, but which, heretofore, appeared to be useless for such applications because of insufficiently satisfactory mechanical properties. The form of the new medullary nail, therefore, had to be one which while using a minimum of material at correspondingly small wall thickness, when compared with known designs, demonstrated adequate tensile and transverse rupture strength and adequate elongation values. Moreover, the form of the medullary nail had to be such that its production is attainable predominantly by chipless shaping, with cold working of originally soft materials. The profile of the inner wall of the tubular nail had to be such that guide spits, such as heretofore normally used, could continue to be used for introducing the nail into the bone.

This problem involving the above-mentioned requirements is solved according to the invention by providing a medullary nail which consists of niobium or tantalum or an alloy containing a predominant amount of one of those metals and which possesses in profile an annular form having a plurality of approximately circular concave zones, the zones being bounded laterally by sharp edges to zones of annular form. In a preferred embodiment of the nail, the tubular body has a zone or area at one end provided with a female thread into which devices or means for driving in or inserting an extracting the medullary nail are screwed.

According to a further preferred embodiment, the surface of the medullary nail is anodically oxidized.

Figure 2:
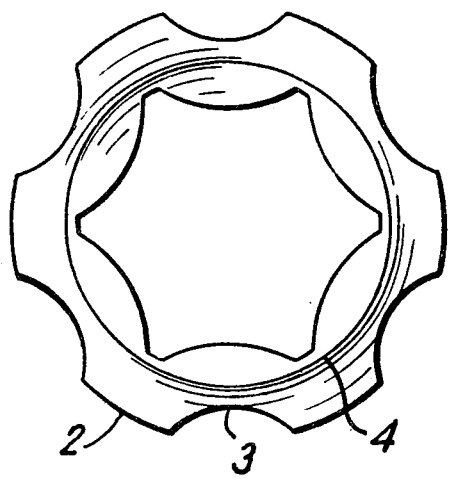

In the Drawing:

FIG. 1 is a view in elevation of a medullary nail according to the invention; and FIG. 2 is a plan view of the nail shown in FIG. 1.

As can be seen in FIG. 1, the medullary nail of the invention tapers downwardly towards the cutter 4. In the outer generated surface, longitudinal, approximately constant grooves are present over the entire length of the nail body. Zones of annular form 2 are contiguous to circular concave zones 3. At the end opposite the cutter, the medullary nail shown has a female thread 1.

The plan view of the top side according to FIG. 2 shows the profile of the medullary nail. The constant wall thickness throughout the entire profile of the nail is striking. This profile form, not previously described in this way, shows that the medullary nail is laid out for high strength and stiffness at as small as possible a wall thickness and, hence, minimum use of material. It can further be seen that the medullary nail has in profile several circular concave zones, bounded by sharp edges to the zones of annular form.

A medullary nail according to the present invention is made of niobium or tantalum. While chromium-molybdenum-nickel steels normally used for such applications have tensile strengths between 600 and 100 N/mm$^2$ and at the same time elongations of 30–45%, comparable values of tensile strength and elongation are not simultaneously attainable for niobium and tantalum. However, for reasons of organic tissue compatibility the medullary nail of niobium or tantalum or an alloy containing a predominant amount of one of these metals is clearly preferable to a medullary nail of the previously described materials.

A first process for the production of medullary nails according to the present invention consists in rolling a sintered body of niobium or tantalum to form a sheet which is then shaped into a slotted tubular form, without the occurrence of fissuring due to brittleness of the material. Thereafter, the body is welded to form a closed tube. Then the final profiling is effected, in particular the forming of the circular concave zones, by rolling with rollers, forging or pressing. Because of the special profile form and the uniform wall thickness of the nail, the material has approximately the same high consolidation throughout. Thus, regions or areas of different deformation and, hence, different strength do not occur. Thus, the internal stresses of the material are low. Unlike steel nails, a niobium or tantalum nail shows no susceptibility to stress corrosion cracking, even if microfissures occur in the material. The shaping of the material can be carried out uniformly in all areas or regions up to a limit strength at which the embrittlement of the niobium or tantalum material, which also increases with the strength, is just still tolerable. Subsequently, the medullary nail is burred on all sides and the generated surfaces polished. Next, the cutting of the female thread and the anodic oxidizing of the material surface is effected.

According to a second process of production, the tubular form of the medullary nail is produced from a sintered body be extrusion of a sheet type starting material in a one-step operation. Thereafter, the tube is brought to smaller diameters by drawing and/or forging. The further production sequence corresponds to the above described production process.

By making the medullary nail according to the described form of the present invention and according to the described manufacturing process, hardness values of 160 to 200 Vickers units and simultaneous elongation values of about 10% can be obtained, for example, when using tantalum as the material. The transverse rupture strength of a medullary nail is decisive in so far as its usefulness is concerned. At equal outside diameter and equal wall thickness, a medullary nail according to the present invention, made of tantalum, shows the same transverse rupture strength as the initially mentioned Küntscher nail. The elastic flexure range for a tantalum nail according to the present invention is actually greater than that of the Küntscher nail of high-alloyed steel.

The medullary nail according to the present invention can be employed with the drilling tools and guide spits normally used with known medullary nails.

With the special form of the medullary nail according to the present invention, the amount of material used can be kept so small, while achieving adequate strength properties, that in the case where niobium is employed as nail material, a weight comparable to the conventional medullary nails made of steel is attainable. The production of a medullary nail of tantalum having the features of the present invention is, from the aspect of material costs, fully justified by its high tissue compatibility. The form of a medullary nail according to the invention results in a nail of a weight which is neither unwieldy nor disadvantageous from the medical point of view.

Due to the sharp-edged boundaries between individual zones, the profile form of the medullary nail according to the present invention shows a very good rotation stability in the bone, without the occurrence of the disadvantages of a nail with elevations that taper outwardly to a point.

We claim:

1. A rotation stable medullary nail for fracture fixation having a hollow body provided with a plurality of longitudinal grooves in the outer surface and a cutter at one end; said longitudinal grooves disposed over the total length of said body to the vicinity of said cutter; said hollow body comprised of a composition selected from the group consisting of tantalum, an alloy of tantalum containing more than 50% by weight tantalum, niobium, and an alloy of niobium containing more than 50% by weight niobium, said hollow body having an inner periphery and an outer periphery, said inner periphery being formed by a closed series of contiguously alternating convex and concave segments of which said concave segments are arranged so as to be tangent to an inscribed circle; said outer periphery being formed by a closed series of contiguously alternating convex and concave segments of which said convex segments are arranged to be colinear with a second circle which is larger than and concentric to said inscribed circle; said concave segments of said inner and outer peripheries being substantially aligned so that said hollow body has a substantially uniform radial cross-sectional dimension extending between said inner periphery and said outer periphery; said radial dimension being substantially the same over the entire length of said nail body; said longitudinal grooves having sharp edges formed by the abutments of said concave and convex segments in said outer periphery.

2. A medullary nail according to claim 1, wherein a female thread (1) is located at the end of the nail body opposite the cutter.

3. A medullary nail according to claim 1, wherein the nail body is superficially anodically oxidized.

* * * * *